United States Patent
Burnham et al.

(10) Patent No.: US 6,365,159 B1
(45) Date of Patent: Apr. 2, 2002

(54) SPO-REL

(76) Inventors: Martin Karl Russel Burnham; Daniel Robert Gentry; John Edward Hodgson; Elizabeth Jane Lawlor, all of SmithKline Beecham Corporation, Corporate Intellectual Property - UW2220, King of Prussia, PA (US) 19406-0939

( * ) Notice: Subject to any disclaimer, the term of this patent is extended or adjusted under 35 U.S.C. 154(b) by 0 days.

(21) Appl. No.: 09/340,475

(22) Filed: Jun. 30, 1999

Related U.S. Application Data

(62) Division of application No. 08/788,892, filed on Jan. 22, 1997, now Pat. No. 5,989,864.
(60) Provisional application No. 60/030,151, filed on Nov. 1, 1996, and provisional application No. 60/029,329, filed on Oct. 29, 1996.

(30) Foreign Application Priority Data

Feb. 26, 1996 (GB) ............................................. 9604045

(51) Int. Cl.⁷ ........................ A61K 39/02; A61K 39/00; A61K 39/385; A61K 39/085; C07K 1/00
(52) U.S. Cl. ................................ 424/190.1; 424/192.1; 424/193.1; 424/197.11; 424/234.1; 424/243.1; 530/350
(58) Field of Search ........................... 424/190.1, 192.1, 424/193.1, 197.11, 234.1, 243.1; 530/350

(56) References Cited

FOREIGN PATENT DOCUMENTS

| EP | 0 786 519 | 7/1997 |
|---|---|---|
| EP | 0 841 394 A | 5/1998 |
| WO | WO 97 30070 | 8/1997 |

OTHER PUBLICATIONS

Gentry, et. al., "Mutational analysis of the *Escherichia coli* spoT gene identifies distinct but overlapping regions involved in ppGpp synthesis and degradation." *Molecular Microbiology*, vol. 19, No. 6, pp. 1373–1384, (1996).

Xiao, et. al., "Residual Guanosine 3', 5'–Bispyrophosphate Synthetic Activity of relA Null Mutants can Be Eliminated by spoY Null Mutations." *The Journal of Biological Chemintry*, vol. 266, No. 9, pp. 5980–5990, Issue of Mar. 25, (1991).

Mechold, et. al., "Genetic organization of the streptokionase region of the *Streptococcus equisimilis* H46A chromosome." *Mol. Gen. Genet,* vol. 241, pp. 129–140, (1993).

Metzger, et. al., Protein Sequences Encoded by the relA and spoT genes of *Escherichia coli* Are Interrelated.' The Journal of Biological Chemistry, Communication, vol. 264, No. 16, pp. 9122–9125, Issue of Jun. 5, (1989).

Mechold, et al., "Functional Analysis of a relA/spoT Gene Homolog from *Streptococcus equisimilis*", *Journal of Bacteriology,* vol. 178, No. 5, pp. 1401–1411, Mar. 1996.

Database Empro2:Sequence SEDEXB AN.X72832, "*Streptococcus equisimilis* dexb, abc, lrp, skc, rel genes and ORF1", Oct. 13, 1993.

Fujimura, et al., "Increase of Methicillin Resistance in *Staphylococcus aureus* Caused by Deletion of a Gene Whose Product is Homologous to Lytic Enzymes", *Journal of Bacteriology,* vol. 179, No. 20, pp. 6294–6301, Oct. 1997.

European Search Report completed Nov. 17, 1999 from corresponding European Application No. 97308503.8, filed Oct. 24, 1997.

Primary Examiner—Albert Navarro

(57) ABSTRACT spo-rel polypeptides and DNA (RNA) encoding such spo-rel and a procedure for producing such polypeptides by recombinant techniques is disclosed. Also disclosed are methods for utilizing such spo-rel for the treatment of infection, particularly bacterial infections. Antagonists against such spo-rel and their use as a therapeutic to treat infections, particularly bacterial infections are also disclosed. Also disclosed are diagnostic assays for detecting diseases related to the presence of spo-rel nucleic acid sequences and the polypeptides in a host. Also disclosed are diagnostic assays for detecting polynucleotides encoding the relA/spoT gene family and for detecting the polypeptide in a host.

6 Claims, 11 Drawing Sheets

FIGURE 1A. spo-rel cloned DNA sequence [SEQ ID NO:1]

```
  1  CTGTTAGAAA AGAAGGGAAA TTACCTCGTG AAGTCATTCG TTATGAGTAT
 51  GACCTAGAAT ATGGTACAAA TGTTTTAACA ATGCACAAAG ATGCAATTAA
101  ACCAGGTCAA CGTGTGTTAA TTACAGATGA TTTATTAGCT ACTGGTGTA
151  CGATTGAAGC AGCAATAAAA TTAGTTGAAA AATTAGGCGG TATCGTAGTA
201  GGTATTGCAT TTATAATTGA ATTGAAATAT TTAAATGGTA TTGAAAAAAT
251  TAAAGATTAC GATGTTATGA GTTTAATCTC ATACGACGAA TAATAAATAA
301  TATAATTTTA TCAAATGAAA TCCTTCATCA AATGTATAAG AACCAATGAC
351  TTAATTAAAA AAGTTGTTTA AGTTTCTTA ATGATTGAGC TTAGGATTTT
401  TTATTACTG AAAATGTTAG ATGATTGAGC ATTATACCTT AATAACATCG
451  TTTATTTATT TCATAAATTG TAGTATCATA GAACTAATAT TTAAAAAATG
501  AAACAGTAGA TTTAGGTCGA ATTTTGTAA AAGTTTAAA AGTAGGAATA
```

Figure 1B

```
551   GTATACAAAT TAAACTCGCT CAAGTAAAAT TAATATTACG ATTAATGACG
601   ACAGGATAAA TATTTATCGT CGACGGACGT ATGATTGGTG TGGGACAAAT
651   ACTATTCAAC AAGAGTACCT AAATCATTGT TTAAGGCGAA GTAATAAATA
701   TGAATGGGGT GTATCATATA ATGAACAACG AATATCCATA TAGTGCAGAT
751   GAAGTTCTTC ACAAAGCAAA ATCATATATTG TCAGCAGATG AATATGAGTA
801   TGTTTTAAAA AGCTATCATA TTGCTTATGA AGCACATAAA GGTCAGTTCC
851   GAAAAAACGG ATTACCATAC ATTATGCATC CTATACAAGT TGCAGGTATT
901   TTAACAGAAA TGCCGATTAGA CGGACCGACG ATTGTCGCAG GTTTTTTGCA
951   TGATGTAATT GAAGATACAC CGTATACATT TGAAGATGTA AAAGAAATGT
1001  TCAATGAAGA AGTTGCTCGA ATTGTTGATG GTGTGACGAA GCTTAAAAAA
1051  GTAAAATACC GCTCAAAAGA AGAACAACAA GCTGAAAATC ATCGCAAGTT
```

Figure 1C

```
1101  ATTTATTGCG ATTGCCAAAG ATGTACGCGT AATTTTGGTG AAATTAGCAG
1151  ACAGATTACA TAATATGCGT ACCTTGAAAG CCATGCCCGCG TGAAAAACAA
1201  ATTAGAATTT CTCGAGAAAC ATTAGAAATT TATGCACCTT TAGCACATCG
1251  TCTTGGTATT AATACAATTA AATGGGAACT AGAAGATACG GCTCTTCGTT
1301  ATATTGATAA TGTGCAATAT TTTAGAATAG TCAATTTAAT GAAGAAGAAA
1351  CGTAGTGAAC GTGAAGCGTA TATCGAAACG GCTATTGATA GAATACGTAC
1401  TGAAATGGAC CGAATGAATA TCGAAGGCGA TATAAATGGT AGACCTAAAC
1451  ATATTTACAG TATTTATCGG AAAAATGATGA AGCAGAAAAA ACAATTTGAT
1501  CAAATTTTTG ATTTGTTGGC GATACGTGTT ATTGTCAATT CTATTAATGA
1551  TTGTTATGCG ATACTTGGGT TGGTGCATAC GTTATGGAAA CCGATGCCAG
1601  GACGTTTTAA AGATTATATT GCAATGCCTA AACAAAATTT GTATCAGTCA
```

Figure 1D

```
1651 TTGCATACTA CAGTAGTAGG TCCAAATGGA GACCCGCTCG AAATCCAAAT
1701 ACGAACGTTT GATATGCACG AAATTGCTGA GCATGGTGTT GCAGCACACT
1751 GGGCTTACAA AGAAGGTAAA AAAGTAAGTG AAAAAGATCA AACTTATCAA
1801 AATAAGTTAA ATTGGTTAAA AGAATTAGCT GAAGCGGATC ATACATCGTC
1851 TGACGCTCAA GAATTTATGG AAACCCTTAAA ATATGACTTA CAGAGTGACA
1901 AAGTATACGC ATTTACCCCA GCGAGTGATG TTATTGAGTT GCCATATGGT
1951 GCTGTGCCGA TTGATTTTGC TTATGCGATT CACAGTGAAG TAGGTAATAA
2001 GATGATTGGT GCCAAGGTGA ATGGCAAAAT TGTACCAATT GACTATATTT
2051 TACAAACAGG CGATATTGTT GAAATACGTA CTAGTAAACA TTCATATGGA
2101 CCAAGTCGTG ATTGGTTGAA AATTGTTAAA TCGTCTAGTG CCAAAGGTAA
2151 AATTAAAAGT TTCTTCAAAA AACAAGATCG TTCATCTAAT ATTGAAAAAG
```

Figure 1E

```
2201  GCCGAATGAT GGTTGAAGTT GAAATAAAAG AGCAAGGATT TAGAGTCGAA
2251  GATATTTTGA CAGAGAAAAA TATTCAGGTT GTTAATGAAA AATATAACTT
2301  TGCAAATGAA GATGATTTAT TCGCAGCTGT AGGATTTGGC GGCGTGACAT
2351  CCTTACAGAT TGTTAATAAA TTAACTGAAA GACAACGTAT TTTAGATAAA
2401  CAACGTGCTT TAAATGAAGC ACAAGAAGTT ACGAAATCAT TGCCTATTAA
2451  AGACAACATC ATTACTGATA GTGGTGTCTA TGTAGAAGGT TTAGAAAATG
2501  TACTTATCAA GTTGTCAAAA TGTTGTAATC CTATACCAGG TGATGATATT
2551  GTAGGTTATA TCACCAAAGG AAGAACGAAA CTGAACGACT AAGTACATC GCACTGATTG
2601  CCCAAATATT AAGAACGAAA CTGAACGACT AATTAATGTT GAATGGGTAA
2651  AATCAAAAGA CGCAACTCAA AAATATCAGG TTGATTTAGA GGTAACTGCG
2701  TATGACCGAA ATGGCTTGTT GAATGAAGTA CTACAAGCTG TTAGCTCGAC
```

Figure 1F

```
2751  AGCCGGGCAAT TTAATTAAAG TTTCAGGACG TTCAGATATT GATAAAAATG
2801  CAATAATAAA TATTAGTGTC ATGGTGAAAA ACGTGAATGA TGTTTATCGT
2851  GTGGTAGAAA AGATCAAACA ACTTGGTGAT GTTTATACAG TAACAAGAGT
2901  TTGGAACTAG AGGTGCAAAA TATGAAAGTA GTTGTACAAA GAG
```

FIGURE 2A. spo-rel predicted amino acid sequence [SEQ ID NO:2]

```
  1  MNGVYHIMNN EYPYSADEVL HKAKSYLSAD EYEYVLKSYH IAYEAHKGQF
 51  RKNGLPYIMH PIQVAGILTE MRLDGPTIVA GFLHDVIEDT PYTFEDVKEM
101  FNEEVARIVD GVTKLKKVKY RSKEEQQAEN HRKLFIAIAK DVRVILVKLA
151  DRLHNMRTLK AMPREKQIRI SRETLEIYAP LAHRLGINTI KWELEDTALR
201  YIDNVQYFRI VNLMKKKRSE REAYIETAID RIRTEMDRMN IEGDINGRPK
251  HIYSIYRKMM KQKKQFDQIF DLLAIRVIVN SINDCYAILG LVHTLWKPMP
301  GRFKDYIAMP KQNLYQSLHT TVVGPNGDPL EIQIRTFDMH EIAEHGVAAH
351  WAYKEGKKVS EKDQTYQNKL NWLKELAEAD HTSSDAQEFM ETLKYDLQSD
401  KVYAFTPASD VIELPYGAVP IDFAYAIHSE VGNKMIGAKV NGKIVPIDYI
451  LQTGDIVEIR TSKHSYGPSR DWLKIVKSSS AKGKIKSFFK KQDRSSNIEK
501  GRMMVEVEIK EQGFRVEDIL TEKNIQVVNE KYNFANEDDL FAAVGFGGVT
```

Figure 2B

551 SLQIVNKLTE RQRILDKQRA LNEAQEVTKS LPIKDNIITD SGVYVEGLEN

601 VLIKLSKCCN PIPGDDIVGY ITKGHGIKVH RTDCPNIKNE TERLINVEWV

651 KSKDATQKYQ VDLEVTAYDR NGLLNEVLQA VSSTAGNLIK VSGRSDIDKN

701 AIINISVMVK NVNDVYRVVE KIKQLGDVYT VTRVWN

FIGURE 3A. [SEQ ID NO:7]

```
  1 CGGCTCTTCG TAATATTGAT AATGTGCAAT ATTTNAAGAA TAATCAATTT
 51 ATTGAAGAAG AAACCGTAGT GACCGTGAGC GAATATCGAA NCGGCTATTG
101 ATAGAATACG TACTGAAATG GACCCGAATG AATATCGAAG NCGATATAAA
151 TGGTAGACCT AAACATATTT ACAGTATTTA TCGGNAAATG ATGAAGCAGA
201 AAAAACAATT TGATCAAATT TTTGATTTGT TGGCGATACG TGTTATTGTC
251 AATTCTATTA ATGATTGTTA TGCGATACTT GGGTTGGTGC ATACGTTATG
301 GAAACCGATG CCAGGACGTT TTAAAGATTA TATTGCAAATG CCTAAACAAA
351 ATTTGTATCA GTCATTGCAT ACTACAGTAG TAGGTCCAAA TGGAGACCCG
401 CTCGAAATCC AAATACGAAC GTTTGATATG CACGAAATTG CTGAGCATGG
451 TGTTGCAGCA CACTGGGCTT ACAAAGAAGG TAAAAAAGTA AGTGAAAAAG
501 ATCAAACTTA TCAAAATAAG TTAAATTGGT TAAAAGAATT AGCTGAAGCG
551 GATCATACAT CGTCTGACGC TCAAGAATTT ATGGAAACCT TATAATATGA
601 CTTACAGAGT GACAAAGTAT ACGCATTTAC CCCAGGGAGT GATGTTATTG
651 AGTNGGCATA TGGTGCTGTG CCGATTGGAT TTTGGCTTAT GCGAATCACA
```

Figure 3B

701 GGGAANGTAG GTAATAAGAT GATTGGCGCC CAGGTGGAAT GGCAAAATTG
751 TACCANATTG ACTTATNTTT TCACAAAACA GGCGGATATT GTTGGAAATA
801 CCGTTCTAG

FIGURE 4. [SEQ ID NO:8]

```
  1  MNIEXDINGR PKHIYSIYRX MMKQKKQFDQ IFDLLAIRVI VNSINDCYAI
 51  LGLVHTLWKP MPGRFKDYIA MPKQNLYQSL HTTVVGPNGD PLEIQIRTFD
101  MHEIAEHGVA AHWAYKEGKK VSEKDQTYQN KLNWLKELAE ADHTSSDAQE
151  FMETL
```

SPO-REL

This application is a divisional of U.S. application Ser. No. 08/788,892, filed Jan. 22, 1997 now U.S. Pat. No. 5,989,864, which claims benefit of provisional application No. 60/030,151, filed Nov. 1, 1996 and provisional application No. 60/029,329, filed Oct. 29, 1996.

This invention relates, in part, to newly identified polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides of the relA/spoT gene family, hereinafter referred to as "spo-rel".

BACKGROUND OF THE INVENTION

The Staphylococci make up a medically important genera of microbes. They are known to produce two types of disease, invasive and toxigenic. Invasive infections are characterized generally by abscess formation effecting both skin surfaces and deep tissues. Staphylococcus aureus is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

This invention provides novel spo-rel, which can be used, among other things, for screening for pharmaceutical compounds to treat Staphylococcal infections. In E. coli relA and spoT proteins are involved in the stringent response to nutrient limitation and regulate the accumulation of (p)ppGpp which is involved in the regulation of gene expression and other cellular processes (see Cashel, M. et al. The Stringent Response. In F. C. Neidhardt et al. (eds) Escherichia coli and Salmonella: cellular and molecular biology, 2n edition, ASM Press, Washington, D.C., 1996). The spoT protein is capable of both the synthesis and degradation of (p)ppGpp while the relA protein is capable of (p)ppGpp synthesis only. The spoT and relA proteins are homologous being 55.6% similar and 31.9% identical (Metzger et al., J. Biol. Chem. 264:9122–9125, 1989).

The genetic organization of the streptokinase region of the Streptococcus equisimilis H46A chromosome has been defined including the sequence of a full length ORF of a relA/spoT homolog, desingated rel (Mechold, U. et al. Mol. Gen. Genet. 241:129–140, 1993). Functional analysis of the rel gene from Streptococcus equisimilis indicates that the encoded protein is similar to E. coli spoT in that it catalyzes both the synthesis and degradation of (p)ppGpp (Mechold, U., et al., J. Bacteriol. 178:1401–1411, 1996).

Clearly, there is a need for factors, such as spo-rel of the invention, that may be used to screen compounds for antibiotic activity and which may also be used to determine their roles in pathogenesis of infection, dysfunction and disease. There is a need, therefore, for identification and characterization of such factors which can play a role in preventing, ameliorating or correcting infections, dysfunctions or diseases.

The polypeptide of the present invention has amino acid sequence homology to known guanosine 3', 5'-bis (diphosphate) synthetase/hydrolase protein.

SUMMARY OF THE INVENTION

Toward these ends, and others, it is an object of the present invention to provide polypeptides, inter alia, that have been identified as novel spo-rel peptides by homology between the amino acid sequence set out in FIG. 2 [SEQ ID NO:2] and known amino acid sequences of other proteins such as Streptococcus equisimilis rel protein protein.

It is a further object of the invention, moreover, to provide polynucleotides that encode spo-rel polypeptides, particularly polynucleotides that encode the polypeptide herein designated spo-rel.

In a particularly preferred embodiment of this aspect of the invention the polynucleotide comprises the region encoding spo-rel polypeptides in the sequence set out in FIG. 1 [SEQ ID NO:1], or a fragment, analogue or derivative thereof.

In another particularly preferred embodiment of the present invention there is a novel guanosine 3', 5'-bis (diphosphate) synthetase/hydrolase protein from Staphylococcus aureus comprising the amino acid sequence of FIG. 2 [SEQ ID NO:2], or a fragment, analogue or derivative thereof.

In accordance with this aspect of the present invention there is provided an isolated nucleic acid molecule encoding a mature polypeptide expressible by the bacterial strain Staphylococcus aureus WCUH 29 contained in NCIMB Deposit No. 40771.

In accordance with this aspect of the invention there are provided isolated nucleic acid molecules encoding spo-rel, particularly Staphylococcus spo-rel, including mRNAs, cDNAs, genomic DNAs and, in further embodiments of this aspect of the invention include biologically, diagnostically, prophylactically, clinically or therapeutically useful variants, analogs or derivatives thereof, or fragments thereof, including fragments of the variants, analogs and derivatives, and compositions comprising same.

In accordance with another aspect of the present invention, there is provided the use of a polynucleotide of the invention for therapeutic or prophylactic purposes, in particular genetic immunization.

Among the particularly preferred embodiments of this aspect of the invention are naturally occurring allelic variants of spo-rel and polypeptides encoded thereby.

In accordance with this aspect of the invention there are provided novel polypeptides of Staphylococcus referred to herein as spo-rel as well as biologically, diagnostically, prophylactically, clinically or therapeutically useful fragments, variants and derivatives thereof, variants and derivatives of the fragments, and analogs of the foregoing, and compositions comprising same.

Among the particularly preferred embodiments of this aspect of the invention are variants of spo-rel polypeptide encoded by naturally occurring alleles of the spo-rel gene.

In a preferred embodiment of this aspect of the invention there are provided methods for producing the aforementioned spo-rel polypeptides.

In accordance with yet another aspect of the present invention, there are provided inhibitors to such polypeptides, useful as antibacterial agents, including, for example, antibodies.

In accordance with certain preferred embodiments of this aspect of the invention, there are provided products, compositions and methods, inter alia: assessing spo-rel expression; to treat diseases and infections of the upper respiratory tract, e.g., otitis media, bacterial tracheitis, acute epiglottitis, thyroiditis), lower respiratory, e.g. empyema, lung abscess, cardiac, e.g. infective endocarditis, gastrointestinal, e.g. secretory diarrhea, splenic abscess, retroperitoneal abscess, CNS, e.g. cerebral abscess, eye, e.g. blepharitis, conjunctivitis, keratitis, endophthalmitis, preseptal & orbital cellulitis, darcryocystitis, kidney and urinary tract, e.g. epididymitis, intrarenal and perinephric abscess, toxic shock syndrome, skin, e.g. impetigo, folliculitis, cutaneous abscesses, cellulitis, wound infection, bacterial myositis, and bone and joint, e.g. septic arthritis, osteomyelitis; assaying genetic variation; and administering a spo-rel polypeptide or polynucleotide to an organism to raise an immunological response against a bacteria, especially a bacteria of the genus Staphylococcus.

In accordance with certain preferred embodiments of this and other aspects of the invention there are provided polynucleotides that hybridize to spo-rel polynucleotide sequences.

In certain additional preferred embodiments of this aspect of the invention there are provided antibodies against spo-rel polypeptides.

In accordance with another aspect of the present invention, there are provided spo-rel agonists which are also preferably bacteriostatic or bacteriocidal.

In accordance with yet another aspect of the present invention, there are provided spo-rel antagonists which are also preferably bacteriostatic or bacteriocidal.

In a further aspect of the invention there are provided compositions comprising a spo-rel polynucleotide or a spo-rel polypeptide for administration to a cell or to a multicellular organism.

Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A–1F shows the polynucleotide sequence of *Staphylococcus aureus* spo-rel [SEQ ID NO:1].

FIGS. 2A–2B shows the amino acid sequence of *Staphylococcus aureus* spo-rel [SEQ ID NO:2] deduced from the polynucleotide sequence of FIG. 1.

FIG. 3A and 3B show a fragment of the polynucleotide sequence of *Staphylococcus aureus* spo-rel [SEQ ID NO:7].

FIG. 4 shows the amino acid fragment of *Staphylococcus aureus* spo-rel [SEQ ID NO:8] deduced from the polynucleotide sequence of FIG. 3A and 3B.

GLOSSARY

The following illustrative explanations are provided to facilitate understanding of certain terms used frequently herein, particularly in the Examples. The explanations are provided as a convenience and are not limitative of the invention.

spo-rel-BINDING MOLECULE, as used herein, refers to molecules or ions which bind or interact specifically with spo-rel polypeptides or polynucleotides of the present invention, including, for example enzyme substrates, cell membrane components and classical receptors. Binding between polypeptides of the invention and such molecules, including binding or binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polynucleotide sequence.

IDENTITY or SIMILARITY, as known in the art, are relationships between two or more polypeptide sequences or two or more polynucleotide sequences, as the case may be, as determined by comparing the sequences. In the art, identity also means the degree of sequence relatedness between polypeptide or polynucleotide sequences, as the case may be, as determined by the match between strings of such sequences. Both identity and similarity can be readily calculated (*Computational Molecular Biology*, Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology,* von Heinje, G., Academic Press, 1987; *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Methods commonly employed to determine identity or similarity between sequences include, but are not limited to those disclosed in Carillo, H., and Lipman, D., SIAM *J. Applied Math.,* 48:1073 (1988). Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J. Molec. Biol.* 215: 403 (1990)).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other posttranslational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS— STRUCTURE AND MOLECULAR PROPERTIES*, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663: 48–62 (1992). It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the NH$_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, E. coli. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination. An "N" in a polynucleotide sequence of the invention means polynucleotides comprising A, C, G or T at this position are included as embodiments of the invention.

DETAILED DESCRIPTION OF THE INVENTION

The present invention relates to novel spo-rel polypeptides and polynucleotides, among other things, as described in greater detail below. In particular, the invention relates to polypeptides and polynucleotides of a novel spo-rel gene of Staphylococcus aureus, which is related by amino acid sequence homology to Streptococcus equisimilis rel protein polypeptide. The invention relates especially to spo-rel having the nucleotide and amino acid sequences set out in FIG. 1 [SEQ ID NO:1] and FIG. 2 [SEQ ID NO:2] respectively, and to the spo-rel nucleotide and amino acid sequences of the DNA in NCIMB Deposit No. 40771, which is herein referred to as "the deposited bacterial strain" or as the "DNA of the deposited bacterial strain." It will be appreciated that the nucleotide and amino acid sequences set out in FIGS. 1 [SEQ ID NO:1] and 2 [SEQ ID NO:2] were obtained by sequencing the DNA of the deposited bacterial strain. Hence, the sequence of spo-rel of the deposited bacterial strain is controlling as to any discrepancies between it (and the sequence it encodes) and the sequences of FIG. 1 [SEQ ID NO: 1] and FIG. 2 [SEQ ID NO:2].

The invention also provides spo-rel having the nucleotide and amino acid sequences set out in FIG. 3 [SEQ ID NO:7] and FIG. 4 [SEQ ID NO:8] respectively Techniques are available to evaluate temporal gene expression in bacteria, particularly as it applies to viability under laboratory and host infection conditions. A number of methods can be used to identify genes which are essential to survival per se, or essential to the establishing/maintenance of an infection. Identification of expression of a sequence by one of these methods yields additional information about its function and permits the selection of such sequence for further development as a screening target. Briefly, these approaches include:

1) Signature Tagged Mutagenesis (STM)

This technique is described by Hensel et al., Science 269: 400–403(1995), the contents of which is incorporated by reference for background purposes. Signature tagged mutagenesis identifies genes necessary for the establishment/maintenance of infection in a given infection model.

The basis of the technique is the random mutagenesis of target organism by various means (e.g., transposons) such that unique DNA sequence tags are inserted in close proximity to the site of mutation. The tags from a mixed population of bacterial mutants and bacteria recovered from an infected hosts are detected by amplification, radiolabeling and hybridization analysis. Mutants attenuated in virulence are revealed by absence of the tag from the pool of bacteria recovered from infected hosts.

In Staphylococcus aureus, because the transposon system is less well developed, a more efficient way of creating the tagged mutants is to use the insertion-duplication mutagenesis technique as described by Morrison et al, J. Bacteriol. 159:870 (1984) the contents of which is incorporated by reference for background purposes.

2) In Vivo Expression Technology (IVET)

This technique is described by Camilli et al., Proc. Nat'l. Acad. Sci. USA. 91:2634–2638 (1994), the contents of which is incorporated by reference for background purposes. IVET identifies genes up-regulated during infection when compared to laboratory cultivation, implying an important role in infection. Sequences identified by this technique are implied to have a significant role in infection establishment/maintenance.

In this technique random chromosomal fragments of target organism are cloned upstream of a promoter-less reporter gene in a plasmid vector. The pool is introduced into a host and at various times after infection bacteria may be recovered and assessed for the presence of reporter gene expression. The chromosomal fragment carried upstream of an expressed reporter gene should carry a promoter or portion of a gene normally upregulated during infection. Sequencing upstream of the reporter gene allows identification of the up regulated gene.

3) Differential Display

This technique is described by Chuang et al, *J. Bacteriol* 175:2026–2036 (1993), the contents of which is incorporated by reference for background purposes. This method identifies those genes which are expressed in an organism by identifying mRNA present using randomly-primed RT-PCR. By comparing pre-infection and post infection profiles, genes up and down regulated during infection can be identified and the RT-PCR product sequenced and matched to library sequences.

4) Generation of conditional lethal mutants by transposon mutagenesis.

This technique, described by de Lorenzo, V. et al, *Gene* 123:17–24 (1993); Neuwald, A. F. et al., *Gene* 125: 69–73 (1993); and Takiff, H. E. et al., *J. Bacteriol.* 174:1544–1553 (1992), the contents of which is incorporated by reference for background purposes, identifies genes whose expression are essential for cell viability.

In this technique transposons carrying controllable promoters, which provide transcription outward from the transposon in one or both directions, are generated. Random insertion of these transposons into target organisms and subsequent isolation of insertion mutants in the presence of inducer of promoter activity ensures that insertions which separate promoter from coding region of a gene whose expression is essential for cell viability will be recovered. Subsequent replica plating in the absence of inducer identifies such insertions, since they fail to survive. Sequencing of the flanking regions of the transposon allows identification of site of insertion and identification of the gene disrupted. Close monitoring of the changes in cellular processes/morphology during growth in the absence of inducer yields information on likely function of the gene. Such monitoring could include flow cytometry (cell division, lysis, redox potential, DNA replication), incorporation of radiochemically labeled precursors into DNA, RNA, protein, lipid, peptidoglycan, monitoring reporter enzyme gene fusions which respond to known cellular stresses.

5) Generation of conditional lethal mutants by chemical mutagenesis.

This technique is described by Beckwith, *J., Methods in Enzymology* 204: 3–18(1991), the contents of which are incorporated herein by reference for background purposes. In this technique random chemical mutagenesis of target organism, growth at temperature other than physiological temperature (permissive temperature) and subsequent replica plating and growth at different temperature (e.g. 42° C. to identify ts, 25° C. to identify cs) are used to identify those isolates which now fail to grow (conditional mutants). As above close monitoring of the changes upon growth at the non-permissive temperature yields information on the function of the mutated gene. Complementation of conditional lethal mutation by library from target organism and sequencing of complementing gene allows matching with library sequences.

Each of these techniques may have advantages or disadvantage depending on the particular application. The skilled artisan would choose the approach that is the most relevant with the particular end use in mind. For example, some genes might be recognised as essential for infection but in reality are only necessary for the initiation of infection and so their products would represent relatively unattractive targets for antibacterials developed to cure established and chronic infections.

6) RT-PCR

Bacterial messenger RNA, preferably that of *Staphylococcus aureus*, is isolated from bacterial infected tissue e.g. 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for novel antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of bacterial 16S ribosomal RNA, preferably that of *Staphylococcus aureus*, as detected by probing Northerns with a suitably labeled sequence specific oligonucleotide probe. Typically a 5', dye labelled primer is used in each PCR primer pair in a PCR reaction which is terminated optimally between 8 and 25 cycles. The PCR products are separated on 6% polyacrylamide gels with detection and quantification using GeneScanner (manufactured by ABI). Using RT-PCR it was determined that the polynucleotide set forth in SEQ ID NO:1 is expressed in vivo.

Use of the of these technologies when applied to the sequences of the present invention enables identification of bacterial protein species expressed during infection, inhibitors of which would have utility in anti-bacterial therapy.

Polynucleotides

In accordance with one aspect of the present invention, there are provided isolated polynucleotides which encode the spo-rel polypeptide having the deduced amino acid sequence of FIG. 2 [SEQ ID NO:2].

Using the information provided herein, such as the polynucleotide sequence set out in FIG. 1 [SEQ ID NO:1], a polynucleotide of the present invention encoding spo-rel polypeptide may be obtained using standard cloning and screening procedures, such as those for cloning and sequencing genomic DNA fragments from *Staphylococcus aureus* WCUH 29 cells as starting material, followed by obtaining a full length clone. For example, to obtain a polynucleotide of the invention sequence, such as that sequence given in FIG. 1 [SEQ ID NO: 1] typically a library of clones of chromosomal DNA of *Staphylococcus aureus* WCUH 29 in *E. coli* or some other suitable host is probed with a radiolabeled oligonucleotide, preferably a 17-mer or longer, derived from a partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., MOLECULAR CLONING, A LABORATORY MANUAL, 2nd Ed.; Cold Spring Harbor Laboratory Press, Cold Spring Harbor, New York (1989). (see Screening By Hybridization 1.90 and Sequencing Denatured Double-Stranded DNA Templates 13.70). Mustrative of the invention, the polynucleotide set out in FIG. 1 [SEQ ID NO:1] was discovered in a DNA library derived from Staphylococcus aureus WCUH 29.

Spo-rel of the invention is structurally related to other proteins of the relA/spoT gene family, as shown by the results of sequencing the DNA encoding spo-rel of the deposited bacterial strain. The DNA sequence thus obtained is set out in FIG. 1 [SEQ ID NO:1]. It contains an open reading frame encoding a protein having about the number of amino acid residues set forth in FIG. 2 [SEQ ID NO:2] with a deduced molecular weight that can be calculated using amino acid residue molecular weight values well known in the art. The protein exhibits greatest homology to Streptococcus equisimilis rel protein protein among known proteins. spo-rel of FIG. 2 [SEQ ID NO:2] has about 50% identity over its entire length and about 69% similarity over its entire length with the amino acid sequence of Streptococcus equisimilis rel protein.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 [SEQ ID NO:1]. It also may be a polynucleotide with a different sequence, which, as a result of the redundancy (degeneracy) of the genetic code, encodes the polypeptide of FIG. 2 [SEQ ID NO:2].

Polynucleotides of the present invention which encode the polypeptide of FIG. 2 [SEQ ID NO:2] may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. Thus, for instance, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., Proc. Natl. Acad. Sci., USA 86: 821–824 (1989), for instance, hexa-histidine provides for convenient purification of the fusion protein. The HA tag may also be used to create fusion proteins and corresponds to an epitope derived of influenza hemagglutinin protein, which has been described by Wilson et al, Cell 37: 767 (1984), for instance. Polynucleotides of the invention also include, but are not limited to, polynucleotides comprising a structural gene and its naturally associated genetic elements.

In accordance with the foregoing, the term "polynucleotide encoding a polypeptide" as used herein encompasses polynucleotides which include a sequence encoding a polypeptide of the present invention, particularly bacterial, and more particularly the Staphylococcus aureus spo-rel having the amino acid sequence set out in FIG. 2 [SEQ ID NO:2]. The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 [SEQ ID NO:2]. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of spo-rel set out in FIG. 2 [SEQ ID NO:2]; variants, analogs, derivatives and fragments thereof, and fragments of the variants, analogs and derivatives.

Further particularly preferred in this regard are polynucleotides encoding spo-rel variants, analogs, derivatives and fragments, and variants, analogs and derivatives of the fragments, which have the amino acid sequence of spo-rel polypeptide of FIG. 2 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of spo-rel. Also especially preferred in this regard are conservative substitutions. Most highly preferred are polynucleotides encoding polypeptides having the amino acid sequence of FIG. 2 [SEQ ID NO:2], without substitutions.

Further preferred embodiments of the invention are polynucleotides that are at least 70% identical over their entire length to a polynucleotide encoding spo-rel polypeptide having the amino acid sequence set out in FIG. 2 [SEQ ID NO:2], and polynucleotides which are complementary to such polynucleotides. Alternatively, most highly preferred are polynucleotides that comprise a region that is at least 80% identical over their entire length to a polynucleotide encoding spo-rel polypeptide of the Staphylococcus aureus DNA of the deposited bacterial strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

The present invention further relates to polynucleotides which hybridize to the hereinabove-described sequences if there is at least 50% and preferably at least 70% identity between the sequences, particularly polynucleotides which hybridize to the polynucleotides set forth in FIG. 3 [SEQ ID NO:7] and/or FIG. 1 [SEQ ID NO:1]. The present invention particularly relates to Staphylococcal polynucleotides which hybridize under stringent conditions to the hereinabove-described polynucleotides, particularly polynucleotides which hybridize to the polynucleotide set forth in FIG. 3 [SEQ ID NO:7] and/or FIG. 1 [SEQ ID NO:1]. As herein used, the term "stringent conditions" means hybridization will occur only if there is at least 95% and preferably at least 97% identity between the sequences.

Preferred embodiments in this respect, moreover, are polynucleotides which encode polypeptides which retain substantially the same biological function or activity as the mature polypeptide encoded by the DNA of FIG. 1 [SEQ ID NO:1], such as, for example, the polypeptide encoded by nucleic acids 700 to 2907 of FIG. 1 [SEQ ID NO: 1].

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding spo-rel and to isolate cDNA and genomic clones of other genes that have a high sequence similarity to the spo-rel gene. Such probes generally will comprise at least 15 bases. Preferably, such probes will have at least 30 bases and may have at least 50 bases. Particularly preferred probes will have at least 30 bases and will have 50 bases or less.

For example, the coding region of the spo-rel gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library the probe hybridizes to.

The polynucleotides and polypeptides of the present invention may be employed as research reagents and materials for discovery of treatments of and diagnostics for disease, particularly human disease, as further discussed herein relating to polynucleotide assays, inter alia.

The polynucleotides of the invention that are oligonucleotides, including SEQ ID NOS:3 and 4, derived from the sequences of SEQ ID NOS: 1 and 2 may be used in the processes herein as described, but preferably for PCR, to determine whether or not the Staphylococcus aureus genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A deposit containing a Staphylococcus aureus bacterial strain (WCUH29) has been deposited with the National Collections of Industrial and Marine Bacteria Ltd. (NCIMB), 23 St. Machar Drive, Aberdeen AB2 IRY, Scotland on Sep. 11, 1995 and assigned NCIMB Deposit No. 40771. The Staphylococcus aureus bacterial strain of the deposit is referred to herein as "the deposited bacterial strain" or as "the DNA of the deposited bacterial strain" and is referred to as "NCIMB 40771" upon deposit.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a spo-rel polypeptide which has a deduced amino acid sequence of 735 amino acids in length, as set forth in FIG. 2 [SEQ ID NO:2], and has a deduced molecular weight of 84,536.52 Daltons.

The invention also relates to fragments, analogs and derivatives of these polypeptides. The terms "fragment," "derivative" and "analog" when referring to the polypeptide of FIG. 2 [SEQ ID NO:2], means a polypeptide which retains essentially the same biological function or activity as such polypeptide. Thus, an analog includes a proprotein which can be activated by cleavage of the proprotein portion to produce an active mature polypeptide.

The fragment, derivative or analog of the polypeptide of FIG. 2 [SEQ ID NO:2] may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of spo-rel set out in FIG. 2 [SEQ ID NO:2], variants, analogs, derivatives and fragments thereof, and variants, analogs and derivatives of the fragments. Alternatively, particularly preferred embodiments of the invention in this regard are polypeptides having the amino acid sequence of the spo-rel, variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the spo-rel polypeptide of FIG. 2 [SEQ ID NO:2], in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the spo-rel. Also especially preferred in this regard are conservative substitutions. Most highly preferred are polypeptides having the amino acid sequence of FIG. 2 [SEQ ID NO:2] without substitutions.

The polypeptides and polynucleotides of the present invention are preferably provided in an isolated form, and preferably are purified to homogeneity.

The polypeptides of the present invention include the polypeptide of FIG. 2 [SEQ ID NO:2] (in particular the mature polypeptide) as well as polypeptides which have at least 70% identity to the polypeptide of FIG. 2 [SEQ ID NO:2], preferably at least 80% identity to the polypeptide of FIG. 2 [SEQ ID NO:2], and more preferably at least 90% similarity (more preferably at least 90% identity) to the polypeptide of FIG. 2 [SEQ ID NO:2] and still more preferably at least 95% similarity (still more preferably at least 95% identity) to the polypeptide of FIG. 2 [SEQ ID NO:2] and also include portions of such polypeptides with such portion of the polypeptide generally containing at least 30 amino acids and more preferably at least 50 amino acids.

The polypeptides of the present invention include the polypeptide of FIG. 4 [SEQ ID NO:8] as well as polypeptides which have at least 70% identity to the polypeptide of FIG. 4 [SEQ ID NO:8], preferably at least 80% identity to the polypeptide of FIG. 4 [SEQ ID NO:8], and more preferably at least 90% similarity (more preferably at least 90% identity) to the polypeptide of FIG. 4 [SEQ ID NO:8] and still more preferably at least 95% similarity (still more preferably at least 95% identity) to the polypeptide of FIG. 4 [SEQ ID NO:8] and also include portions of such polypeptides with such portion of the polypeptide generally containing at least 30 amino acids and more preferably at least 50 amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of spo-rel, most particularly fragments of spo-rel having the amino acid set out in FIG. 2 [SEQ ID NO:2], and fragments of variants and derivatives of the spo-rel of FIG. 2 [SEQ ID NO:2].

In this regard a fragment is a polypeptide having an amino acid sequence that entirely is the same as part but not all of the amino acid sequence of the aforementioned spo-rel polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a spo-rel polypeptide of the present comprised within a precursor polypeptide designed for expression in a host and having heterologous pre and pro-polypeptide regions fused to the amino terminus of the spo-rel fragment and an additional region fused to the carboxyl terminus of the fragment. Therefore, fragments in one aspect of the meaning intended herein, refers to the portion or portions of a fusion polypeptide or fusion protein derived from spo-rel.

Representative examples of polypeptide fragments of the invention, include, for example, fragments from about amino acid number 1–20, 21–40, 41–60, 61–80, 81–100, and in 20 amino acid increments from 101–735, and any combination of any of these 20 amino acid fragments. In this context "about" herein includes the particularly recited ranges larger or smaller by several, a few, 5, 4, 3, 2 or 1 amino acid at either extreme or at both extremes.

Preferred fragments of the invention include, for example, truncation polypeptides of spo-rel. Truncation polypeptides include spo-rel polypeptides having the amino acid sequence of FIG. 2 [SEQ ID NO:2], or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally. Degradation forms of the polypeptides of the invention in a host cell, particularly a Staphylococcus, are also preferred.

Also preferred in this aspect of the invention are fragments characterized by structural or functional attributes of spo-rel. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions of spo-rel, and combinations of such fragments.

Preferred regions are those that mediate activities of spo-rel. Most highly preferred in this regard are fragments that have a chemical, biological or other activity of spo-rel, including those with a similar activity or an improved activity, or with a decreased undesirable activity. Further preferred polypeptide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, Host Cells, Expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989).

Polynucleotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbor, New York (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the E. coli lac, trp and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., *MOLECULAR CLONING, A LABORATORY MANUAL*, 2nd Ed.; Cold Spring Harbor Laboratory Press, Cold Spring Harbor, New York (1989).

Representative examples of appropriate hosts include bacterial cells, such as streptococci, staphylococci, *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSK3 pBPV, pMSG and pSVL available from Pharmacia These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunolglobulin that is useful to solubilize or purify polypeptides. For example, EP-A-O 464 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See, D. Bennett et al., *Journal of Molecular Recognition*, Vol. 8 52–58 (1995) and K. Johanson et al, *The Journal of Biological Chemistry*, Vol. 270, No. 16, pp 9459–9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation regions, splice donor and acceptor sites, transcriptional termination sequences, and 5' flanking non-transcribed sequences that are necessary for expression.

spo-rel polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding protein may be employed to regenerate active conformation when the polypeptide is denatured during isolation and or purification.

Polynucleotide Assays

This invention is also related to the use of the spo-rel polynucleotides to detect complementary polynucleotides such as, for example, as a diagnostic reagent. Detection of spo-rel in a eukaryote, particularly a mammal, and especially a human, will provide a diagnostic method for diagnosis of a disease. Eukaryotes (herein also "individual(s)"), particularly mammals, and especially humans, infected with an organism comprising the spo-rel gene may be detected at the DNA level by a variety of techniques. Nucleic acids for diagnosis may be obtained from an infected individual's cells and tissues, such as bone, blood, muscle, cartilage, and skin. Genomic DNA may be used directly for detection or may be amplified enzymatically by using PCR (Saiki et al., *Nature,* 324: 163–166 (1986) prior to analysis. RNA or cDNA may also be used in the same ways. As an example, PCR primers complementary to the nucleic acid encoding spo-rel can be used to identify and analyze spo-rel presence and/or expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled spo-rel RNA or alternatively, radiolabeled spo-rel antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic characterization based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science,* 230: 1242 (1985)).

Sequence changes at specific locations also may be revealed by nuclease protection assays, such as RNase and S1 protection or the chemical cleavage method (e.g., Cotton et al., *Proc. Natl, Acad. Sci.,* USA, 85: 4397–4401(1985)).

Thus, the detection of a specific DNA sequence may be achieved by methods such as hybridization, RNase protection, chemical cleavage, direct DNA sequencing or the use of restriction enzymes, e.g., restriction fragment length polymorphisms (RFLP) and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding spo-rel can be used to identify and analyze mutations. Examples of representative primers are shown below in Table

TABLE 1

Primers used for amplification of spo-rel polynucleotides

| SEQ ID NO | PRIMER SEQUENCE |
|---|---|
| 3 | 5'-CCGCCATGGGTAACAACGAATATCCATATAGT-3' |
| 4 | 5'-CGGGATCCGCACCTCTAGTTCCAAACTCT-3' |
| 5 | 5'-agatacgtac tgaaatgg-3' |
| 6 | 5'-cctgtgattc gcataagc-3' |

These primers may be used for amplifying spo-rel DNA isolated from a sample derived from an individual. The invention also provides the primers of Table 1 with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be diagnosed.

The invention provides a process for diagnosing, disease, preferably bacterial infections, more preferably *Staphylococcus aureus*, and most preferably upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis), comprising determining from a sample derived from an individual a increased level of expression of polynucleotide having the sequence of FIG. 1 [SEQ ID NO: 1]. Increased expression of spo-rel polynucleotide can be measured using any on of the methods well known in the art for the quantation of polynucleotides, such as, for example, PCR, RT-PCR, RNase protection, Northern blotting and other hybridization methods.

Polypeptide Assays

The present invention also relates to a diagnostic assays such as quantitative and diagnostic assays for detecting levels of spo-rel protein in cells and tissues, including determination of normal and abnormal levels. Thus, for instance, a diagnostic assay in accordance with the invention for detecting over-expression of spo-rel protein compared to normal control tissue samples may be used to detect the presence of an infection, for example. Assay techniques that can be used to determine levels of a spo-rel protein, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to spo-rel, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONO-CLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope-termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against spo-rel may be employed to inhibit and/or treat infections, particularly bacterial infections and especially upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis).

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognised by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanized"; where the complimentarily determining region(s) of the hybridoma-derived antibody has been transplanted into a human monoclonal antibody, for example as described in Jones, P. et al. (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem 1989:264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

spo-rel-binding Molecules and Assays

This invention also provides a method for identification of molecules, such as binding molecules, that bind spo-rel. Genes encoding proteins that bind spo-rel, can be identified by numerous methods known to those of skill in the art, for example, ligand panning and FACS sorting. Such methods are described in many laboratory manuals such as, for instance, Coligan et al, *Current Protocols in Immunology* 1(2): Chapter 5 (1991). Also, a labeled ligand can be photoaffinity linked to a cell extract.

Polypeptides of the invention also can be used to assess spo-rel binding capacity of spo-rel-binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Antagonists and Agonists—Assays and Molecules

The invention also provides a method of screening compounds to identify those which enhance (agonist) or block (antagonist) the action of spo-rel polypeptides or polynucleotides, such as its interaction with spo-rel-binding molecules.

For example, to screen for agonists or antagonists, a synthetic reaction mix, a cellular compartment, such as a membrane, cell envelope or cell wall, or a preparation of any thereof, may be prepared from a cell that expresses a molecule that binds spo-rel. The preparation is incubated with labeled spo-rel in the absence or the presence of a candidate molecule which may be a spo-rel agonist or antagonist. The ability of the candidate molecule to bind the binding molecule is reflected in decreased binding of the labeled ligand. Molecules which bind gratuitously, i.e., without inducing the effects of spo-rel on binding the spo-rel binding molecule, are most likely to be good antagonists. Molecules that bind well and elicit effects that are the same as or closely related to spo-rel are agonists.

spo-rel-like effects of potential agonists and antagonists may by measured, for instance, by determining activity of a reporter system following interaction of the candidate molecule with a cell or appropriate cell preparation, and comparing the effect with that of spo-rel or molecules that elicit the same effects as spo-rel. Reporter systems that may be useful in this regard include but are not limited to colorimetric labeled substrate converted into product, a reporter gene that is responsive to changes in spo-rel activity, and binding assays known in the art.

Another example of an assay for spo-rel antagonists is a competitive assay that combines spo-rel and a potential antagonist with membrane-bound spo-rel-binding molecules, recombinant spo-rel binding molecules, natural substrates or ligands, or substrate or ligand mimetics, under appropriate conditions for a competitive inhibition assay. spo-rel can be labeled, such as by radioactivity or a colorimetric compound, such that the number of spo-rel molecules bound to a binding molecule or converted to product can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing spo-rel-induced activities, thereby preventing the action of spo-rel by excluding spo-rel from binding.

Potential antagonists include a small molecule which binds to and occupies the binding site of the polypeptide thereby preventing binding to cellular binding molecules, such that normal biological activity is prevented. Examples of small molecules include but are not limited to small organic molecules, peptides or peptide-like molecules.

Other potential antagonists include antisense molecules (see Okano, *J. Neurochem* 56: 560 (1991); *OLIGODEOXYNUCLEOTIDES AS ANTISENSE INHIBITORS OF GENE EXPRESSION,* CRC Press, Boca Raton, Fla. (1988), for a description of these molecules). Other potential antagonists also include compounds related to and derivatives of spo-rel.

In a particular aspect the invention provides the use of the polypeptide, polynucleotide or inhibitor of the invention to interfere with the initial physical interaction between a pathogen and mammalian host responsible for sequelae of infection. In particular the molecules of the invention may be used: i) in the prevention of adhesion of bacteria, in particular gram positive bacteria, to mammalian extracellular matrix proteins on in-dwelling devices or to extracellular matrix proteins in wounds; ii) to block guanosine 3', 5'-bis (diphosphate) synthetase/hydrolase protein mediated mammalian cell invasion by, for example, initiating phosphorylation of mammalian tyrosine kinases (Rosenshine et al, *Infect, Immun.* 60:2211 (1992); iii) to block bacterial adhesion between mammalian extracellular matrix proteins and bacterial guanosine 3', 5'-bis(diphosphate) synthetase/hydrolase proteins which mediate tissue damage; iv) to block the normal progression of pathogenesis in infections initiated other than by the implantation of in-dwelling devices or by other surgical techniques.

Each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists may be employed for instance to inhibit upper respiratory tract (e.g. otitis media, bacterial tracheitis, acute epiglottitis, thyroiditis), lower respiratory (e.g. empyema, lung abscess),cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal & orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis)

Vaccines

Another aspect of the invention relates to a method for inducing an immunological response in an individual, particularly a mammal which comprises inoculating the individual with spo-rel, or a fragment or variant thereof, adequate to produce antibody to protect said individual from infection, particularly bacterial infection and most particularly Staphylococcus infections. Yet another aspect of the invention relates to a method of inducing immunological response in an individual which comprises, through gene therapy, delivering gene encoding spo-rel, or a fragment or a variant thereof, for expressing spo-rel, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a spo-rel or protein coded therefrom, wherein the composition comprises a recombinant spo-rel or protein coded therefrom comprising DNA which codes for and expresses an antigen of said spo-rel or protein coded therefrom.

The spo-rel or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of *Staphylococcus aureus* infection in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain spo-rel, it is to be understood that this covers fragments of the naturally occurring protein and similar proteins with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent Staphylococcus wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10mg/ml for bathing of wounds or indwelling devices.

A vaccine composition is conveniently in injectable form. Conventional adjuvants may be employed to enhance the immune response.

A suitable unit dose for vaccination is 0.5–5 µg/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing the guanosine 3', 5'-bis(diphosphate) synthetase/hydrolase protein.

In order to facilitate understanding of the following example certain frequently occurring methods and/or terms will be described.

EXAMPLES

The present invention is further described by the following examples. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL*, 2nd Ed.; Cold Spring Harbor Laboratory Press, Cold Spring Harbor, N.Y. (1989).

Example 1

Library Production

The polynucleotide having the DNA sequence given in SEQ ID NO: 1 was obtained from a library of clones of chromosomal DNA of *Staphylococcus aureus* in *E. coli*. In some cases the sequencing data from two or more clones containing overlapping *Staphylococcus aureus* DNAs was used to construct the contiguous DNA sequence in SEQ ID NO:1. Libraries may be prepared by routine methods, for example: Methods 1 and 2 below.

Total cellular DNA is isolated from *Staphylococcus aureus* WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

Complementation of an *E. coli* ppGpp-less Strain

An *E. coli* mutant lacking both ppGpp synthetases, encoded by the relA and spoT genes, cannot grow in the absence of amino acid supplementation (Xiao et al., 1991). Any expressed gene that encodes a ppGpp synthetase is expected to provide sufficient ppGpp to allow growth on media lacking amino acids (Gentry and Cashel, 1996; Mechold et al. 1996). A *Staphylococcus areus* spo-rel gene is cloned into pBluescript and transformed into an *E. coli* Dre/A DspoT strain (Xiao et al., 1991). Resulting transformants are screened for their ability to grow on M63 medium supplemented with glucose (0.2%). Complementation is scored after 16 h growth at 37° C.

Example 2

References

Gentry, D. R., and M. Cashel. 1996. Mutational analysis of the *Escherichia coli* spoT gene identifies distinct but overlapping regions involved in ppGpp synthesis and degradation. Mol. Microbiol. 19:1373–1384.

Mechold, U., M. Cashel, K. Steiner, D. Gentry, and H. Malke. 1996. Functional analysis of a relA/spoT gene homolog of *Streptococcus equisimilis*. J. Bacteriol. 178:1401–1411.

Xiao, H., M. Kalman, K. Ikehara, S. Zemel, G. Glaser, and M. Cashel. 1991. Residual guanosine 3', 5'-bispyrophosphate synthetic activity of a relA null mutants can be eliminated by spoT null mutations. J. Biol. Chem. 266: 5980–5990.

Example 3

The Determination of Expression During Infection of a Gene from *Staphylococcus aureus*

Necrotic fatty tissue from a four day groin infection of *Staphylococcus aureus* WCUH29 in the mouse is efficiently disrupted and processed in the presence of chaotropic agents and RNAase inhibitor to provide a mixture of animal and bacterial RNA. The optimal conditions for disruption and processing to give stable preparations and high yields of bacterial RNA are followed by the use of hybridisation to a radiolabelled oligonucleotide specific to *Staphylococcus aureus* 16S RNA on Northern blots. The RNAase free, DNAase free, DNA and protein free preparations of RNA obtained are suitable for Reverse Transcription PCR (RT-PCR) using unique primer pairs designed from the sequence of each gene of *Staphylococcus aureus* WCUH29.

a) Isolation of Tissue Infected with *Staphylococcus aureus* WCUH29 from a Mouse Animal Model of Infection 10 ml. volumes of sterile nutrient broth (No.2 Oxoid) are seeded with isolated, individual colonies of *Staphylococcus aureus* WCUH29 from an agar culture plate. The cultures are incubated aerobically (static culture) at 37° C. for 16–20 hours. 4 week old mice (female, 18 g–22 g, strain MF1) are each infected by subcutaneous injection of 0.5 ml. of this broth culture of *Staphylococcus aureus* WCUH29 (diluted in broth to approximately $10^8$ cfu/ml.) into the anterior, right lower quadrant (groin area). Mice should be monitored regularly during the first 24 hours after infection, then daily until termination of study. Animals with signs of systemic infection, i.e. lethargy, ruffled appearance, isolation from group, should be monitored closely and if signs progress to moribundancy, the animal should be culled immediately.

Visible external signs of lesion development will be seen 24–48 h after infection. Examination of the abdomen of the animal will show the raised outline of the abscess beneath the skin. The localised lesion should remain in the right lower quadrant, but may occasionally spread to the left lower quadrant, and superiorly to the thorax. On occasions, the abscess may rupture through the overlying skin layers. In such cases the affected animal should be culled immediately and the tissues sampled if possible. Failure to cull the animal may result in the necrotic skin tissue overlying the abscess being sloughed off, exposing the abdominal muscle wall.

Approximately 96 hours after infection, animals are killed using carbon dioxide asphyxiation. To minimise delay between death and tissue processing /storage, mice should be killed individually rather than in groups. The dead animal is placed onto its back and the fur swabbed liberally with 70% alcohol. An initial incision using scissors is made through the skin of the abdominal left lower quadrant, travelling superiorly up to, then across the thorax. The incision is completed by cutting inferiorly to the abdominal lower right quadrant. Care should be taken not to penetrate the abdominal wall. Holding the skin flap with forceps, the skin is gently pulled way from the abdomen. The exposed abscess, which covers the peritoneal wall but generally does not penetrate the muscle sheet completely, is excised, taking care not to puncture the viscera The abscess/muscle sheet and other infected tissue may require cutting in sections, prior to flash-freezing in liquid nitrogen, thereby allowing easier storage in plastic collecting vials.

b) Isolation of *Staphylococcus Aureus* WCUH29 RNA from Infected Tissue Samples

4–6 infected tissue samples(each approx 0.5–0.7g) in 2 ml screw-cap tubes are removed from −80° C. storage into a dry ice ethanol bath In a microbiological safety cabinet the samples are disrupted individually whilst the remaining samples are kept cold in the dry ice ethanol bath. To disrupt the bacteria within the tissue sample 1 ml of TRIzol Reagent (Gibco BRL, Life Technologies) is added followed by enough 0.1 mm zirconia/silica beads to almost fill the tube, the lid is replaced taking care not to get any beads into the screw thread so as to ensure a good seal and eliminate aerosol generation. The sample is then homogenised in a Mini-BeadBeater Type BX-4 (Biospec Products). Necrotic fatty tissue is strain treated for 100 seconds at 5000 rpm in order to achieve bacterial lysis. In vivo grown bacteria require longer treatment than in vitro grown *Staphylococcus aureus* Staphylococcus which are disrupted by a 30 second bead-beat.

After bead-beating the tubes are chilled on ice before opening in a fume-hood as heat generated during disruption may degrade the TRIzol and release cyanide.

200 microliters of chloroform is then added and the tubes shaken by hand for 15 seconds to ensure complete mixing. After 2–3 minutes at room temperature the tubes are spun down at 12,000×g, 4° C. for 15 minutes and RNA extraction is then continued according to the method given by the manufacturers of TRIzol Reagent i.e.:—The aqueous phase, approx 0.6 ml, is transferred to a sterile eppendorf tube and 0.5 ml of isopropanol is added. After 10 minutes at room temperature the samples are spun at 12,000×g, 4° C. for 10 minutes. The supernatant is removed and discarded then the RNA pellet is washed with 1 ml 75% ethanol. A brief vortex is used to mix the sample before centrifuging at 7,500×g, 4° C. for 5 minutes. The ethanol is removed and the RNA pellet dried under vacuum for no more than 5 minutes. Samples are then resuspended by repeated pipetting in 100 microliters of DEPC treated water, followed by 5–10 minutes at 55° C. Finally, after at least 1 minute on ice, 200 units of Rnasin (Promega) is added.

RNA preparations are stored at −80° C. for up to one month. For longer term storage the RNA precipitate can be stored at the wash stage of the protocol in 75% ethanol for at least one year at −20° C.

Quality of the RNA isolated is assessed by running samples on 1% agarose gels. 1×TBE gels stained with ethidium bromide are used to visualise total RNA yields. To demonstrate the isolation of bacterial RNA from the infected tissue 1×MOPS, 2.2M formaldehyde gels are run and vacuum blotted to Hybond-N (Amersham). The blot is then hybridised with a $^{32}$P labelled oligonucletide probe specific to 16s rRNA of *Staphylococcus aureus* ( K. Greisen, M. Loeffelholz, A. Purohit and D. Leong. J.Clin. (1994) Microbiol. 32 335–351 An oligonucleotide selected from Table 1 is used as a probe. The size of the hybridising band is compared to that of control RNA isolated from in vitro grown *Staphylococcus aureus* WCUH29 in the Northern blot. Correct sized bacterial 16s rRNA bands can be detected in total RNA samples which show extensive degradation of the mammalian RNA when visualised on TBE gels.

c) The removal of DNA from *Staphylococcus aureus* WCUH29-derived RNA

DNA was removed from 73 microliter samples of RNA by a 15 minute treatment on ice with 3 units of DNAaseI, amplification grade (Gibco BRL, Life Technologies) in the buffer supplied with the addition of 200 units of Rnasin (Promega) in a final volume of 90 microliters.

The DNAase was inactivated and removed by treatment with TRIzol LS Reagent (Gibco BRL, Life Technologies) according to the manufacturers protocol. DNAase treated RNA was resuspended in 73 microliters of DEPC treated water with the addition of Rnasin as described in Method 1.

d) The Preparation of cDNA from RNA Samples Derived from Infected Tissue 10 microliter samples of DNAase treated RNA are reverse transcribed using SuperScript Preamplification System for First Strand cDNA Synthesis kit (Gibco BRL, Life Technologies) according to the manufacturers instructions. 1 nanogram of random hexamers is used to prime each reaction. Controls without the addition of SuperScriptII reverse transcriptase are also run. Both+/–RT samples are treated with RNaseH before proceeding to the PCR reaction e) The Use of PCR to Determine the Presence of a Bacterial cDNA Species PCR reactions are set up on ice in 0.2 ml tubes by adding the following components: 45 microliters PCR SUPERMIX (Gibco BRL, Life Technologies); 1 microlitre 50 mM MgCl$_2$, to adjust final concentration to 2.5 mM; 1 microlitre PCR primers(optimally 18–25 basepairs in length and designed to possess similar annealing temperatures), each primer at 10 mM initial concentration; and 2 microlitres cDNA.

PCR reactions are run on a Perkin Elmer GeneAmp PCR System 9600 as follows: 5 minutes at 95° C., then 50 cycles of 30 seconds each at 94° C., 42° C. and 72° C. followed by 3 minutes at 72° C. and then a hold temperature of 4° C. (the number of cycles is optimally 30–50 to determine the appearance or lack of a PCR product and optimally 8–30 cycles if an estimation of the starting quantity of cDNA from the RT reaction is to be made); 10 microlitre aliquots are then run out on 1% 1×TBE gels stained with ethidium bromide with PCR product, if present, sizes estimated by comparison to a 100 bp DNA Ladder (Gibco BRL, Life Technologies). Alternatively if the PCR products are conveniently labelled by the use of a labelled PCR primer (e.g. labelled at the 5' end with a dye) a suitable aliquot of the PCR product is run out on a polyacrylamide sequencing gel and its presence and quantity detected using a suitable gel scanning system (e.g. ABI Prism™377 Sequencer using GeneScan™ software as supplied by Perkin Elmer).

RT/PCR controls may include +/– reverse transcriptase reactions, 16s rRNA primers or DNA specific primer pairs designed to produce PCR products from non-transcribed *Staphylococcus aureus* WCUH29 genomic sequences.

To test the efficiency of the primer pairs they are used in DNA PCR with *Staphylococcus aureus* WCUH29 total DNA. PCR reactions are set up and run as described above using approx. 1 microgram of DNA in place of the cDNA and 35 cycles of PCR.

Primer pairs which fail to give the predicted sized product in either DNA PCR or RT/PCR are PCR failures and as such are uninformative. Of those which give the correct size product with DNA PCR two classes are distinguished in RT/PCR: 1.Genes which are not transcribed in vivo reproducibly fail to give a product in RT/PCR; and 2.Genes which are transcribed in vivo reproducibly give the correct size product in RT/PCR and show a stronger signal in the +RT samples than the signal (if at all present) in -RT controls.

The polynucleotide sequence set forth in [SEQ ID NO: 1] was identified in the above test as being transcribed in vivo. Deduced amino acid sequence is given as SEQ ID NO:2. The pair of PCR primers used to identify the gene are given as SEQ ID NOS:5 and 6. Primers of SEQ ID NO: 3 and 4 may be similarly used.

What is claimed is:

1. An isolated polypeptide comprising SEQ ID NO:2.

2. A composition comprising the isolated polypeptide of claim 1 and a carrier.

3. The isolated polypeptide of claim 1, wherein the isolated polypeptide further comprises a heterologous amino acid sequence.

4. A composition comprising the isolated polypeptide of claim 3 and a carrier.

5. The isolated polypeptide of claim 1, wherein the isolated polypeptide consists of SEQ ID NO:2.

6. A composition comprising the isolated polypeptide of claim 5 and a carrier.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 2943 base pairs
          (B) TYPE: nucleic acid
          (C) STRANDEDNESS: double
          (D) TOPOLOGY: linear (ii) MOLECULE TYPE: Genomic DNA (xi) SEQUENCE DESCRIPTION: SEQ ID NO:1:

CTGTTAGAAA AGAAGGGAAA TTACCTCGTG AAGTCATTCG TTATGAGTAT GACCTAGAAT    60

-continued

```
ATGGTACAAA TGTTTTAACA ATGCACAAAG ATGCAATTAA ACCAGGTCAA CGTGTGTTAA    120

TTACAGATGA TTTATTAGCT ACTGGTGGTA CGATTGAAGC AGCAATAAAA TTAGTTGAAA    180

AATTAGGCGG TATCGTAGTA GGTATTGCAT TTATAATTGA ATTGAAATAT TTAAATGGTA    240

TTGAAAAAAT TAAAGATTAC GATGTTATGA GTTTAATCTC ATACGACGAA TAATAAATAA    300

TATAATTTTA TCAAATGAAA TCCTTCATCA AATGTATAAG AACCAATGAC TTAATTAAAA    360

AAGTTGTTTA AGTTTTCTTA ACATGAGATG TTAGGATTTT TTATTTACTG AAAATGTTAG    420

ATGATTGAGC ATTATACCTT AATAACATCG TTTATTTATT TCATAAATTG TAGTATCATA    480

GAACTAATAT TTAAAAAATG AAACAGTAGA TTTAGGTCGA ATTTTTGTAA AAGTTTTAAA    540

AGTAGGAATA GTATACAAAT TAAACTCGCT CAAGTAAAAT TAATATTACG ATTAATGACG    600

ACAGGATAAA TATTTATCGT CGACGGACGT ATGATTGGTG TGGGACAAAT ACTATTCAAC    660

AAGAGTACCT AAATCATTGT TTAAGGCGAA GTAATAAATA TGAATGGGGT GTATCATATA    720

ATGAACAACG AATATCCATA TAGTGCAGAT GAAGTTCTTC ACAAAGCAAA ATCATATTTG    780

TCAGCAGATG AATATGAGTA TGTTTTAAAA AGCTATCATA TTGCTTATGA AGCACATAAA    840

GGTCAGTTCC GAAAAAACGG ATTACCATAC ATTATGCATC CTATACAAGT TGCAGGTATT    900

TTAACAGAAA TGCGATTAGA CGGACCGACG ATTGTCGCAG GTTTTTTGCA TGATGTAATT    960

GAAGATACAC CGTATACATT TGAAGATGTA AAAGAAATGT TCAATGAAGA AGTTGCTCGA   1020

ATTGTTGATG GTGTGACGAA GCTTAAAAAA GTAAAATACC GCTCAAAAGA GAACAACAA    1080

GCTGAAAATC ATCGCAAGTT ATTTATTGCG ATTGCCAAAG ATGTACGCGT AATTTTGGTG   1140

AAATTAGCAG ACAGATTACA TAATATGCGT ACCTTGAAAG CCATGCCGCG TGAAAAACAA   1200

ATTAGAATTT CTCGAGAAAC ATTAGAAATT TATGCACCTT TAGCACATCG TCTTGGTATT   1260

AATACAATTA AATGGGAACT AGAAGATACG GCTCTTCGTT ATATTGATAA TGTGCAATAT   1320

TTTAGAATAG TCAATTTAAT GAAGAAGAAA CGTAGTGAAC GTGAAGCGTA TATCGAAACG   1380

GCTATTGATA GAATACGTAC TGAAATGGAC CGAATGAATA TCGAAGGCGA TATAAATGGT   1440

AGACCTAAAC ATATTTACAG TATTTATCGG AAAATGATGA AGCAGAAAAA ACAATTTGAT   1500

CAAATTTTTG ATTTGTTGGC GATACGTGTT ATTGTCAATT CTATTAATGA TTGTTATGCG   1560

ATACTTGGGT TGGTGCATAC GTTATGGAAA CCGATGCCAG GACGTTTTAA AGATTATATT   1620

GCAATGCCTA AACAAAATTT GTATCAGTCA TTGCATACTA CAGTAGTAGG TCCAAATGGA   1680

GACCCGCTCG AAATCCAAAT ACGAACGTTT GATATGCACG AAATTGCTGA GCATGGTGTT   1740

GCAGCACACT GGGCTTACAA AGAAGGTAAA AAAGTAAGTG AAAAAGATCA AACTTATCAA   1800

AATAAGTTAA ATTGGTTAAA AGAATTAGCT GAAGCGGATC ATACATCGTC TGACGCTCAA   1860

GAATTTATGG AAACCTTAAA ATATGACTTA CAGAGTGACA AGTATACGC ATTTACCCCA    1920

GCGAGTGATG TTATTGAGTT GCCATATGGT GCTGTGCCGA TTGATTTTGC TTATGCGATT   1980

CACAGTGAAG TAGGTAATAA GATGATTGGT GCCAAGGTGA ATGGCAAAAT TGTACCAATT   2040

GACTATATTT TACAAACAGG CGATATTGTT GAAATACGTA CTAGTAAACA TTCATATGGA   2100

CCAAGTCGTG ATTGGTTGAA AATTGTTAAA TCGTCTAGTG CCAAAGGTAA AATTAAAAGT   2160

TTCTTCAAAA AACAAGATCG TTCATCTAAT ATTGAAAAAG GCCGAATGAT GGTTGAAGTT   2220

GAAATAAAAG AGCAAGGATT TAGAGTCGAA GATATTTTGA CAGAGAAAAA TATTCAGGTT   2280

GTTAATGAAA AATATAACTT TGCAAATGAA GATGATTTAT TCGCAGCTGT AGGATTTGGC   2340

GGCGTGACAT CCTTACAGAT TGTTAATAAA TTAACTGAAA GACAACGTAT TTTAGATAAA   2400

CAACGTGCTT TAAATGAAGC ACAAGAAGTT ACGAAATCAT TGCCTATTAA AGACAACATC   2460
```

-continued

```
ATTACTGATA GTGGTGTCTA TGTAGAAGGT TTAGAAAATG TACTTATCAA GTTGTCAAAA    2520

TGTTGTAATC CTATACCAGG TGATGATATT GTAGGTTATA TCACCAAAGG TCACGGTATT    2580

AAAGTACATC GCACTGATTG CCCAAATATT AAGAACGAAA CTGAACGACT AATTAATGTT    2640

GAATGGGTAA AATCAAAAGA CGCAACTCAA AAATATCAGG TTGATTTAGA GGTAACTGCG    2700

TATGACCGAA ATGGCTTGTT GAATGAAGTA CTACAAGCTG TTAGCTCGAC AGCCGGCAAT    2760

TTAATTAAAG TTTCAGGACG TTCAGATATT GATAAAAATG CAATAATAAA TATTAGTGTC    2820

ATGGTGAAAA ACGTGAATGA TGTTTATCGT GTGGTAGAAA AGATCAAACA ACTTGGTGAT    2880

GTTTATACAG TAACAAGAGT TTGGAACTAG AGGTGCAAAA TATGAAAGTA GTTGTACAAA    2940

GAG                                                                  2943
```

(2) INFORMATION FOR SEQ ID NO:2:

(i) SEQUENCE CHARACTERISTICS:
        (A) LENGTH: 736 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Asn Gly Val Tyr His Ile Met Asn Asn Glu Tyr Pro Tyr Ser Ala
 1               5                  10                  15

Asp Glu Val Leu His Lys Ala Lys Ser Tyr Leu Ser Ala Asp Glu Tyr
                20                  25                  30

Glu Tyr Val Leu Lys Ser Tyr His Ile Ala Tyr Glu Ala His Lys Gly
            35                  40                  45

Gln Phe Arg Lys Asn Gly Leu Pro Tyr Ile Met His Pro Ile Gln Val
        50                  55                  60

Ala Gly Ile Leu Thr Glu Met Arg Leu Asp Gly Pro Thr Ile Val Ala
 65                  70                  75                  80

Gly Phe Leu His Asp Val Ile Glu Asp Thr Pro Tyr Thr Phe Glu Asp
                85                  90                  95

Val Lys Glu Met Phe Asn Glu Glu Val Ala Arg Ile Val Asp Gly Val
                100                 105                 110

Thr Lys Leu Lys Lys Val Lys Tyr Arg Ser Lys Glu Glu Gln Gln Ala
            115                 120                 125

Glu Asn His Arg Lys Leu Phe Ile Ala Ile Ala Lys Asp Val Arg Val
        130                 135                 140

Ile Leu Val Lys Leu Ala Asp Arg Leu His Asn Met Arg Thr Leu Lys
145                 150                 155                 160

Ala Met Pro Arg Glu Lys Gln Ile Arg Ile Ser Arg Glu Thr Leu Glu
                165                 170                 175

Ile Tyr Ala Pro Leu Ala His Arg Leu Gly Ile Asn Thr Ile Lys Trp
            180                 185                 190

Glu Leu Glu Asp Thr Ala Leu Arg Tyr Ile Asp Asn Val Gln Tyr Phe
        195                 200                 205

Arg Ile Val Asn Leu Met Lys Lys Leu Arg Ser Glu Arg Glu Ala Tyr
    210                 215                 220

Ile Glu Thr Ala Ile Asp Arg Ile Arg Thr Glu Met Asp Arg Met Asn
225                 230                 235                 240

Ile Glu Gly Asp Ile Asn Gly Arg Pro Lys His Ile Tyr Ser Ile Tyr
                245                 250                 255
```

-continued

```
Arg Lys Met Met Lys Gln Lys Gln Phe Asp Gln Ile Phe Asp Leu
            260                 265                 270
Leu Ala Ile Arg Val Ile Val Asn Ser Ile Asn Asp Cys Tyr Ala Ile
            275                 280                 285
Leu Gly Leu Val His Thr Leu Trp Lys Pro Met Pro Gly Arg Phe Lys
            290                 295                 300
Asp Tyr Ile Ala Met Pro Lys Gln Asn Leu Tyr Gln Ser Leu His Thr
305                 310                 315                 320
Thr Val Val Gly Pro Asn Gly Asp Pro Leu Glu Ile Gln Ile Arg Thr
                325                 330                 335
Phe Asp Met His Glu Ile Ala Glu His Gly Val Ala Ala His Trp Ala
            340                 345                 350
Tyr Lys Glu Gly Lys Lys Val Ser Glu Lys Asp Gln Thr Tyr Gln Asn
            355                 360                 365
Lys Leu Asn Trp Leu Lys Glu Leu Ala Glu Ala Asp His Thr Ser Ser
            370                 375                 380
Asp Ala Gln Glu Phe Met Glu Thr Leu Lys Tyr Asp Leu Gln Ser Asp
385                 390                 395                 400
Lys Val Tyr Ala Phe Thr Pro Ala Ser Asp Val Ile Glu Leu Pro Tyr
                405                 410                 415
Gly Ala Val Pro Ile Asp Phe Ala Tyr Ala Ile His Ser Glu Val Gly
            420                 425                 430
Asn Lys Met Ile Gly Ala Lys Val Asn Gly Lys Ile Val Pro Ile Asp
            435                 440                 445
Tyr Ile Leu Gln Thr Gly Asp Ile Val Glu Ile Arg Thr Ser Lys His
            450                 455                 460
Ser Tyr Gly Pro Ser Arg Asp Trp Leu Lys Ile Val Lys Ser Ser Ser
465                 470                 475                 480
Ala Lys Gly Lys Ile Lys Ser Phe Phe Lys Lys Gln Asp Arg Ser Ser
                485                 490                 495
Asn Ile Glu Lys Gly Arg Met Met Val Glu Val Glu Ile Lys Glu Gln
            500                 505                 510
Gly Phe Arg Val Glu Asp Ile Leu Thr Glu Lys Asn Ile Gln Val Val
            515                 520                 525
Asn Glu Lys Tyr Asn Phe Ala Asn Glu Asp Asp Leu Phe Ala Ala Val
            530                 535                 540
Gly Phe Gly Gly Val Thr Ser Leu Gln Ile Val Asn Lys Leu Thr Glu
545                 550                 555                 560
Arg Gln Arg Ile Leu Asp Lys Gln Arg Ala Leu Asn Glu Ala Gln Glu
                565                 570                 575
Val Thr Lys Ser Leu Pro Ile Lys Asp Asn Ile Ile Thr Asp Ser Gly
            580                 585                 590
Val Tyr Val Glu Gly Leu Glu Asn Val Leu Ile Lys Leu Ser Lys Cys
            595                 600                 605
Cys Asn Pro Ile Pro Gly Asp Asp Ile Val Gly Tyr Ile Thr Lys Gly
            610                 615                 620
His Gly Ile Lys Val His Arg Thr Asp Cys Pro Asn Ile Lys Asn Glu
625                 630                 635                 640
Thr Glu Arg Leu Ile Asn Val Glu Trp Val Lys Ser Lys Asp Ala Thr
                645                 650                 655
Gln Lys Tyr Gln Val Asp Leu Glu Val Thr Ala Tyr Asp Arg Asn Gly
            660                 665                 670
```

```
Leu Leu Asn Glu Val Leu Gln Ala Val Ser Ser Thr Ala Gly Asn Leu
        675                 680                 685

Ile Lys Val Ser Gly Arg Ser Asp Ile Asp Lys Asn Ala Ile Ile Asn
        690                 695                 700

Ile Ser Val Met Val Lys Asn Val Asn Asp Val Tyr Arg Val Val Glu
705                 710                 715                 720

Lys Ile Lys Gln Leu Gly Asp Val Tyr Thr Val Thr Arg Val Trp Asn
        725                 730                 735
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

CCGCCATGGG TAACAACGAA TATCCATATA GT                    32

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:4:

CGGGATCCGC ACCTCTAGTT CCAAACTCT                      29

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:5:

AGATACGTAC TGAAATGG                                  18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

CCTGTGATTC GCATAAGC                                  18

(2) INFORMATION FOR SEQ ID NO:7:

(i) SEQUENCE CHARACTERISTICS:
        (A) LENGTH: 809 base pairs
        (B) TYPE: nucleic acid
        (C) STRANDEDNESS: double (D) TOPOLOGY: linear (ii) MOLECULE TYPE: Genomic DNA (xi) SEQUENCE DESCRIPTION: SEQ ID NO:7:

```
CGGCTCTTCG TAATATTGAT AATGTGCAAT ATTTNAAGAA TAATCAATTT ATTGAAGAAG      60

AAACCGTAGT GACCGTGAGC GAATATCGAA NCGGCTATTG ATAGAATACG TACTGAAATG     120

GACCCGAATG AATATCGAAG NCGATATAAA TGGTAGACCT AAACATATTT ACAGTATTTA     180

TCGGNAAATG ATGAAGCAGA AAAAACAATT TGATCAAATT TTTGATTTGT TGGCGATACG     240

TGTTATTGTC AATTCTATTA ATGATTGTTA TGCGATACTT GGGTTGGTGC ATACGTTATG     300

GAAACCGATG CCAGGACGTT TTAAAGATTA TATTGCAATG CCTAAACAAA ATTTGTATCA     360

GTCATTGCAT ACTACAGTAG TAGGTCCAAA TGGAGACCCG CTCGAAATCC AAATACGAAC     420

GTTTGATATG CACGAAATTG CTGAGCATGG TGTTGCAGCA CACTGGGCTT ACAAAGAAGG     480

TAAAAAGTA AGTGAAAAAG ATCAAACTTA TCAAATAAG TTAAATTGGT TAAAAGAATT      540

AGCTGAAGCG GATCATACAT CGTCTGACGC TCAAGAATTT ATGGAAACCT TATAATATGA     600

CTTACAGAGT GACAAAGTAT ACGCATTTAC CCCAGGGAGT GATGTTATTG AGTNGGCATA     660

TGGTGCTGTG CCGATTGGAT TTTGGCTTAT GCGAATCACA GGGAANGTAG GTAATAAGAT     720

GATTGGCGCC CAGGTGGAAT GGCAAAATTG TACCANATTG ACTTATNTTT TCACAAAACA     780

GGCGGATATT GTTGGAAATA CCGTTCTAG                                      809
```

(2) INFORMATION FOR SEQ ID NO:8:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Asn Ile Glu Xaa Asp Ile Asn Gly Arg Pro Lys His Ile Tyr Ser
  1               5                  10                  15

Ile Tyr Arg Xaa Met Met Lys Gln Lys Lys Gln Phe Asp Gln Ile Phe
             20                  25                  30

Asp Leu Leu Ala Ile Arg Val Ile Val Asn Ser Ile Asn Asp Cys Tyr
         35                  40                  45

Ala Ile Leu Gly Leu Val His Thr Leu Trp Lys Pro Met Pro Gly Arg
     50                  55                  60

Phe Lys Asp Tyr Ile Ala Met Pro Lys Gln Asn Leu Tyr Gln Ser Leu
 65                  70                  75                  80

His Thr Thr Val Val Gly Pro Asn Gly Asp Pro Leu Glu Ile Gln Ile
                 85                  90                  95

Arg Thr Phe Asp Met His Glu Ile Ala Glu His Gly Val Ala Ala His
            100                 105                 110

Trp Ala Tyr Lys Glu Gly Lys Lys Val Ser Glu Lys Asp Gln Thr Tyr
        115                 120                 125

Gln Asn Lys Leu Asn Trp Leu Lys Glu Leu Ala Glu Ala Asp His Thr
    130                 135                 140

Ser Ser Asp Ala Gln Glu Phe Met Glu Thr Leu
145                 150                 155
```